(12) United States Patent
Baum et al.

(10) Patent No.: US 6,846,424 B2
(45) Date of Patent: Jan. 25, 2005

(54) PLASMA-ASSISTED DRY ETCHING OF NOBLE METAL-BASED MATERIALS

(75) Inventors: Thomas H. Baum, New Fairfield, CT (US); Phillip Chen, Bethel, CT (US); Frank DiMeo, Jr., Danbury, CT (US); Peter C. Van Buskirk, Newtown, CT (US); Peter S. Kirlin, Austin, TX (US)

(73) Assignee: Advanced Technology Materials, Inc., Danbury, CT (US)

(*) Notice: Subject to any disclaimer, the term of this patent is extended or adjusted under 35 U.S.C. 154(b) by 485 days.

(21) Appl. No.: 09/874,102

(22) Filed: Jun. 5, 2001

(65) Prior Publication Data

US 2001/0024679 A1 Sep. 27, 2001

Related U.S. Application Data

(63) Continuation-in-part of application No. 09/453,995, filed on Dec. 3, 1999, which is a continuation-in-part of application No. 08/966,797, filed on Nov. 10, 1997, now Pat. No. 6,018,065, and a continuation-in-part of application No. 09/093,291, filed on Jun. 8, 1998, now Pat. No. 6,254,792.

(51) Int. Cl.$^7$ .............................................. H01L 21/00
(52) U.S. Cl. ............................ 216/13; 216/65; 216/66; 216/67; 216/75; 134/1.1; 134/2; 134/21; 438/694; 438/708; 438/710; 438/720
(58) Field of Search .............................. 216/13, 65, 66, 216/67, 75, 1.1, 2, 21; 438/694.708, 710, 720

(56) References Cited

U.S. PATENT DOCUMENTS

| | | | |
|---|---|---|---|
| 4,659,426 A | | 4/1987 | Fuller et al. |
| 5,492,855 A | * | 2/1996 | Matsumoto et al. ........ 438/396 |
| 5,575,888 A | * | 11/1996 | Kosakowski et al. ......... 216/37 |
| 5,814,238 A | | 9/1998 | Ashby et al. |
| 5,854,104 A | * | 12/1998 | Onishi et al. ............... 438/240 |
| 5,911,887 A | | 6/1999 | Smith et al. |
| 5,976,928 A | | 11/1999 | Van Buskirk et al. |
| 6,018,065 A | | 1/2000 | Baum et al. |
| 2002/0066532 A1 | * | 6/2002 | Shih et al. ................ 156/345.1 |

FOREIGN PATENT DOCUMENTS

| | | | | |
|---|---|---|---|---|
| JP | 56023752 A | * | 3/1981 | ........... H01L/21/88 |

OTHER PUBLICATIONS

Derwent Acc. No. 1981–29945D, May 1981.*
Koteki, D.E., "A Review of High Dielectric Materials for DRAM Capacitors", *Integ. Ferro.*, 1997, vol. 16, pp. 1–19.
Jeon et al., "Thermal Stability of Ir/Polycrystalline–Si Structure for Bottom Electrode of Integrated Ferroelectric Capacitors", *Appl. Physics Lett.*, vol. 71(4), pp. 467–469.
Williams, et al., "Etch Rates for Micromachining Processing", *Journ. For Microelectromechanical Systems*, Dec. 1996, vol. 5 (4), pp. 256–269.

Vugts, et al., "Si/XeF$_2$ Etching–Temperature Dependence", 1996, *J. Vac. Sci. Tech. A*, vol. 14(5), pp. 2766–2774.
P.C. Fazan, et al., "Stacked Capacitor Modules for 64 Mb DRAMs and Beyond", *Semiconductor Inter.*, 1992, vol. 108, pp. 108—112.
L. H. Parker, et al., Ferroelectric Materials for 64Mb and 256Mb DRAMs, *IEEE Circuits and Devices Mag.*, Jan. 1990, pp. 17–26.
R. E. Sievers, et al., "Volatile Barium B–Diketonates for Use as MOCVD Precursors", *Coord. Chem. Rev.*, 1993, pp. 285–291.
C. Farrell, et al., "A Reactive Ion Etch Study for Producing Patterned Platinum Structures", Presented at ISIF 96, Mar. 18, 19,20, 1996 Tempe AZ. (to be published in Integrated Ferroelectrics).
K. R. Milkove and C. X. Wang, "Insight into the dry cleaning of Fence Patterned Platinum Structures", *J. Vac. Sci. Tech. A*, 1997, vol. 15(3), pp. 596–603.
Chang, F.I., et al., "Gas Phase Silicon Micromachining with Xenon Difluoride", *Proc of SPIE*, 1995, vol. 2641, pp. 117–128.
Bensaola, A. et al., "Low Temperature Ion Beam Enhanced Etching of Tungsten Films with Xenon Difluoride", *Appl. Phys. Lett.*, Dec. 1986, vol. 49(24), pp. 1663–1664.
G. Stauf, BaSrTiO3 Etching for Advanced Microelectronic Devices, U.S. Army Missile Command, Report No., DAAH01–96–C–R035, Jan. 10, 1996–Jan. 30, 1998.
Ebsworth, E.A.V., et al., "Formation of Iridium Fluoroacyl Complexes by Reaction of Iridium Carbonyls with Xenon Difluoride and Reactions of these to Generate Unusual Acyl Complexes",*J. Chem. Soc. , Dalton Trans.*, 1993, ISS. 7, pp. 1031–1037.
Blake, A.J., et al., " Novel Reaction of an Iridium Carbonyl Complex with Xenon Difluoride: The First Metal Fluoroacyl Complex",*J. Chem. Soc.*, Chem. Commun., 1988, ISS.8, pp. 529–530.
Sladkey, F.O., et al., "Xenon Difluoride as a Fluoride Ion Donor" *J. Chem. Soc. A*, 1969, vol. 14, pp. 2179–2188.
Floy I. Chang, et al., Gas–Phase Silicon Micromachining with Xenon Difluoride, Proc. Of SPIE vol. 2641, pp. 117–128.

* cited by examiner

Primary Examiner—Allan Olsen
(74) Attorney, Agent, or Firm—Margaret Chappuis; Steven Hultquist, Esq.

(57) ABSTRACT

A process for removing and/or dry etching noble metal-based material structures, e.g., iridium for electrode formation for a microelectronic device. Etch species are provided by plasma formation involving energization of one or more halogenated organic and/or inorganic substance, and the etchant medium including such etch species and oxidizing gas is contacted with the noble metal-based material under etching conditions. The plasma formation and the contacting of the plasma with the noble metal-based material can be carried out in a downstream microwave processing system to provide processing suitable for high-rate fabrication of microelectronic devices and precursor structures in which the noble metal forms an electrode, or other conductive element or feature of the product article.

48 Claims, No Drawings

PLASMA-ASSISTED DRY ETCHING OF NOBLE METAL-BASED MATERIALS

CROSS REFERENCE TO RELATED APPLICATIONS

This application is a continuation-in-part of co-pending U.S. application Ser. No. 09/453,995, filed on Dec. 3, 1999, which is a continuation-in part of U.S. application Ser. No. 08/966,797, filed on Nov. 10, 1997 and issued on Jan. 25, 2000 as U.S. Pat. No. 6,018,065; and a continuation-in-part of U.S. application Ser. No. 09/093,291, filed on Jun. 8, 1998, now U.S. Pat. No. 6,254,792. +gi

GOVERNMENT RIGHTS IN INVENTION

Some aspects of this invention were made in the performance of U.S. Government Contract No. DDAL01-97-C-0079, "BST Capacitors for Cryogenic Focal Plane Arrays;" NIST ATP Program, 70NANB9H3018. The U.S. Government has certain rights in the invention hereof.

BACKGROUND OF THE INVENTION

1. Field of the Invention

The present invention generally relates to a process for removal of noble metal-based materials, and more particularly in a preferred aspect to "dry" etching of deposited iridium-based materials to fabricate microelectronic device structures.

2. Description of the Related Art

Iridium (Ir) and iridium oxide ($IrO_2$) are of great interest for use as electrode materials in both dynamic random access memories (DRAMs) and for ferroelectric-based memory devices (e.g., FRAMs) that incorporate perovskite metal oxide thin-films as the capacitor layer.

The advantages of Ir over other possible electrode materials include ease of deposition, e.g., using chemical vapor deposition (CVD), the ability to "dry" etch the material, the ability to form a stable conducting oxide ($IrO_2$) at high temperatures in an oxidizing environment, the ability to convert $IrO_2$ back to Ir metal at suitable temperatures (on the order of 350° C.) in forming gas, and the ability of the corresponding product microelectronic device to operate stably at high temperatures with a high degree of reliability.

The deposition and/or processing of Ir-based electrodes is highly desirable based on the above-discussed advantages. Ir displays a resistivity 5.3 $\mu\Omega$-cm at 20°C. and $IrO_2$ is highly conducting with a reported resistivity of 100 $\mu\Omega$-cm. The formation of $IrO_2$ occurs only at elevated temperatures (>550°C.) in $O_2$ and is a superior material for the deposition of complex oxides for dielectric or ferroelectric capacitors. Further, during the high temperature CVD process for the growth of these capacitors, the formation of $IrO_2$ can be advantageous for limiting inter-diffusion, as for example by acting as a diffusion barrier to oxidation of conducting polysilicon vias or plugs. $IrO_2$ therefore is a material having many advantages in forming a robust, low-leakage electrode for reliable device fabrication.

Based on the need for Ir-based electrodes, a facile etching method for Ir is critical for commercial manufacturing processes, particularly those involving CVD techniques, since CVD enables the fabrication of electrode structures having dimensional characteristics below 0.5 micron.

In order to obtain useful electrode structures, it generally is necessary to etch the deposited Ir-based material, to form elements of a desired dimensional and locational character. Heretofore, "dry" etching techniques utilizing plasma for reactive ion etching (RIE) have been generally chlorine-based and resulted in significant residue being left on the structure after completion of the etching process.

Depending on the type of structure being formed, such post-etch residue can result in short circuiting, undesirable topography and/or other deficiencies in the subsequent operation of the product microelectronic device. Prevention of the formation of such residues can be achieved in some instances by manipulating the reactive ion etching (RIE) process parameters, but such process manipulation produces undesirable sidewall slopes in the microelectronic device structure that in turn prevent useful submicron capacitors from being fabricated from iridium-based materials.

Accordingly, it would be a significant advance in the art of fabricating microelectronic devices and precursor structures therefor, to provide a simple and commercially useful "dry" etch methodology applicable to Ir-based materials that provides high etching rates, superior etching uniformity and effective control over the shape of the etched features.

SUMMARY OF THE INVENTION

The present invention relates in one aspect to a method for removing residue from or "dry" etching a noble metal material previously deposited on a substrate, such as a microelectonic device, by contacting the deposited material with a gas-phase composition comprising at least one energized halogenated organic and/or inorganic compound or mixture thereof, thereby etching or removing the deposited material to yield a desired structure formed of the noble metal material, e.g., an electrode or other structural component or feature of a microelectronic device.

The gas-phase composition or plasma contacting is advantageously carried out in an "oxidizing ambient environment" for a sufficient time and under sufficient conditions to effectively etch the deposited noble metal material or remove noble metal residue, thereby reducing deficiencies in the operation of the microelectronic device.

The method of the present invention is usefully employed for etching or removing noble metal materials including, without limitation, platinum, palladium, iridium, rhodium and materials comprising alloys or combinations of such metals, as well as alloys or combinations of one or more of such metals with other (non-noble) metal. Most preferably, the noble metal material is an iridium-based material.

As used herein, the term "Ir-based" or "iridium-based" refers broadly to elemental iridium, iridium oxide and iridium-containing material compositions including iridium alloys. As used herein, the term "microelectronic device structure" refers to a microelectronic device, or a precursor structure that must be subjected to subsequent processing or treatment steps to fabricate a final product device.

As used herein, the term "dry" etch refers to etching that is carried out using gaseous reagents, as opposed to wet-etching methods in which liquid-phase reagents are employed to effect material removal from a deposited metal thin film, or layer of material. The "dry" etch process of the present invention is a plasma etching process. A "plasma" is a highly ionized gas with a nearly equal number of positive and negative charged particles plus free radicals. The free radicals are electrically neutral atomic or molecular species that can actively form chemical bonds.

In the plasma etching process or residue removal process of the present invention, free radicals generated in a plasma and acting as a reactive species, chemically combine with materials to be etched or removed and form volatile compounds that are readily removable from the system, e.g., by an evacuating device joined in closed flow communication with the plasma etch chamber.

The reactive etching reagent may include, for example, at least one halogenated compound selected from an organic halogenated compound, such as $C_2F_6$; inorganic halogenated compound, such as $XeF_2$ and $SF_6$ or a mixture of halogenated organic and inorganic compounds, such as $C_2F_6$ and $XeF_2$, and an oxidizing gas to a sufficient amount of energy to generate reactive species sufficiently energized to etch the deposited iridium-based material upon contact therewith.

The halogenated organic compounds that are useful as "starting material" for plasma generation to form the etching medium, can comprise any compound that will effectively provide, upon energizing, a reactive halogenated etching gas. Suitable halogenated organic compounds useful in specific applications of the plasma etching process include, without limitation, alkyl halides having an alkyl moiety selected from $C_1$–$C_6$ alkyl species, with at least some and preferably all of the hydrogen substituents of the alkyl moiety being replaced by halogen. Specific examples of alkyl halides include, without limitation, $CF_4$, $C_2F_6$, $C_2Cl_3F_3$, $C_4F_8$, $C_5F_8$, $C_3F_8$, $C_2Cl_2F_4$, $C_2ClF_3$, $CClF_3$, $CClF_3F$, $CCl_2F_2$, etc., with $C_2F_6$ being a particularly preferred alkyl halide species. The halogenated organic compound can include any suitable halogen substituent, e.g., fluorine, bromine, chlorine, or iodine, with fluorine generally being the most preferred.

In one aspect, an etching gas mixture is employed for the etching of the noble metal-based material, in which the etching gas mixture includes (i) at least one halogenated organic compound and (ii) at least one gas that provides an "oxidizing ambient environment" to assist in the volatilization and removal of iridium product species from the iridium-based material on the substrate.

As used herein, the term "oxidizing ambient environment" means an environment including oxygen-containing gas, such as oxygen ($O_2$), ozone ($O_3$), air, nitrogen oxide (NO), nitrous oxide ($N_2O$), carbon monoxide (CO) or the like, and preferably $O_2$. Such oxidizing atmosphere may be provided in a processing chamber with the introduction of the halogenated organic compound into the chamber to effect the etching of the noble metal-based material.

In one specific embodiment of the dry plasma etching process, the product etched structure, such as for example an electrode or other component of a microelectronic device, is formed with a microwave or radio frequency (RF)-generated etching plasma. Any suitable RF or microwave radiation may be used for plasma generation. In one embodiment of such process, the halogenated compound(s), in an oxidizing ambient environment, is energized in a RF-processing system to produce the plasma for the etch operation.

In another embodiment of the present invention, the product etched structure is formed with a microwave-generated etching plasma. Any suitable microwave radiation may be used for plasma generation.

Other aspects, features and embodiments of the invention will be more fully apparent from the ensuing disclosure and appended claims.

DETAILED DESCRIPTION OF THE INVENTION AND PREFERRED EMBODIMENTS THEREOF

The present invention is based on the discovery that noble metal-based materials, e.g., iridium, platinum, palladium, and rhodium and based electrode structures, can be readily formed into a desired configuration by employing a "dry" etch processing technique on the noble metal-based material, e.g., by utilizing reactive etching gases comprising halogenated organic and/or inorganic compounds in an oxidizing ambient environment.

While the ensuing discussion herein is sometimes hereinafter directed illustratively to iridium as the noble metal forming the deposit to be etchingly altered, it will be appreciated that the invention is not thus limited in utility, but that the invention contemplates plasma etching generally of noble metal-based materials, of which iridium is a widely used species for fabrication of electrodes and other conductive elements and features of microelectronic device articles and precursor structures.

Accordingly, with reference to iridium as a noble metal species illustrative of the method of the invention, the iridium initially can be deposited on the substrate in any suitable manner, including chemical vapor deposition, liquid delivery, sputtering, ablation, or any other suitable technique known in the art for deposition of such metal on a substrate from a metal organic or other precursor or source material. Among the foregoing techniques, chemical vapor deposition is preferred when the iridium-based structures to be formed have critical dimensions below about 0.5 microns. In the deposition of Ir-based materials on a substrate by chemical deposition methods, the precursor for the chemical vapor deposition of the iridium component may be any suitable iridium precursor compound, complex, or composition that is advantageous for yielding iridium during the deposition process.

Prior to contacting of the deposited noble metal-based material on the substrate, the noble metal may be masked, or patterned, e.g., by conventional photoresist or other patterning technique(s), to form a lithographically or otherwise defined pattern for subsequent etch processing.

Etching of the deposited Ir-based material is carried out by contacting the deposited iridium-based material with a reactive etching reagent. The reactive etching reagent may include, for example, at least one halogenated compound selected from an organic halogenated compound, such as $C_2F_6$; inorganic halogenated compound, such as $XeF_2$ and $SF_6$ or a mixture of halogenated organic and inorganic compounds, such as $C_2F_6$ and $XeF_2$, and an oxidizing gas to a sufficient amount of energy to generate reactive species sufficiently energized to etch the deposited iridium-based material upon contact therewith. The contacting of the deposited Ir-based material with the reactive species is carried out for a sufficient time and under sufficient conditions to form an etched surface structure of the desired configuration.

The dry clean process of the present invention may be carried out at any suitable process conditions, including ambient temperature, low temperature and elevated temperature regimes, as well as varying pressure regimes. For example, the cleaning process may be carried out at room temperature conditions involving the sublimation of $XeF_2$ to generate same as an active cleaning agent. $XeF_2$ may also be first reacted with another compound, such as silicon, to generate an active cleaning agent comprising $SiF_2$ radicals.

The time and contacting conditions for the reactive halide etch process may be readily determined by those of ordinary skill in the art. The nature and extent of the etching of the deposited noble metal-based material may be empirically determined while varying the time and/or contacting conditions (such as temperature, pressure, and concentration (partial pressure) of the etching agent to identify the process conditions producing a desired etching result.

The halogenated organic compound can comprise any compound that will effectively provide, upon energizing, a reactive halogenated etching gas. The halogenated organic compound can include, for example, one or more alkyl halides, e.g., $C_1$–$C_6$ alkyl halides such as $CF_4$, $C_2F_6$, $C_2Cl_3F_3$, $C_4F_8$, $C_5F_8$, $C_3F_8$, $C_2Cl_2F_4$, $C_2ClF_3$, $CClF_3$, $CCl_3F$, $CCl_2F_2$, etc., with $C_2F_6$ being highly preferred as a source halocompound to form the etching medium. The halogenated organic compound may comprise any suitable halogen substituent(s), e.g., fluorine, bromine, chlorine, and/or iodine, with fluorine generally being the most preferred. The halogenated organic compound may be partially or fully halogenated, with fully (halo)substituted compounds being preferred, and perfluorocompounds being most preferred.

Advantageously, especially in the case of iridium and/or iridium oxide as the noble metal on the substrate, the etching gas mixture includes the halogenated organic compound in combination with at least one oxygen-containing gas, to assist in the volatilization and removal of iridium product species from the iridium-based material on the substrate. The oxygen-containing gas may include, for example, one or more of $O_2$, $O_3$, $N_2O$, CO, NO, etc. Preferably, the oxygen-containing gas is $O_2$, $O_3$ or a mixture thereof.

While not wishing to be bound by any specific theory of operation, it is believed that the inclusion of an oxygen-containing gas may be advantageous with the use of halogenated organic compounds, to reduce the amount of free carbon available (by reaction of carbonaceous species with the oxygen-containing gas to form CO and $CO_2$).

This substantially prevents any formed polymeric by-products from depositing on the interior surface of the chamber or the etched surfaces. Additionally, any formed CO gas is available to increase etch rates; for example, in applications where the halo species, X=chlorine or bromine, the presence of CO gas serves to enhance the reactant volatility through the formation of $(CO)yIrX_3$ and $Ir(Cl)_4$.

The source gas mixture for the etchant medium therefore comprises a halogenated organic compound, e.g., $C_2F_6$, and an oxidizing gas, e.g., $O_2$, and may be energized in any suitable manner, such as in a RF or microwave processing system.

There are two fundamental types of microwave plasma processing systems, the oven type and the downstream type. The oven type microwave plasma processing system provides a single chamber wherein the plasma generating and reacting regions are combined. The article to be etched is placed in the single chamber and exposed not only to the generated plasma but also to the radiation source. Alternatively, and preferably, a downstream type of microwave plasma processing system, having separated generating and reaction regions, is employed, wherein the workpiece is placed outside of the plasma generating region in the downstream reacting region. This downstream processing type of microwave plasma processing system is preferred because the workpiece is not exposed to the electromagnetic radiation necessary to energize the etching gases.

Owing to the fact that downstream microwave plasma processing is preferred in the general practice of the invention when microwave energization of the source gas(es) is employed for plasma formation, the ensuing description in respect of plasma processing refers to the preferred downstream microwave processing.

In the plasma processing system, the illustrative reactive gas mixture of $C_2F_6$ and $O_2$, whose components may be added either simultaneously or separately to the process chamber, is introduced to the plasma generating chamber and ionized by microwave to form a plasma. The continuous volumetric flow ratio of $C_2F_6$ to $O_2$ in such process can for example be on the order of from about 100 to about 0.1, and more preferably from about 4 to about 0.5.

Radicals generated in the plasma generating region of the microwave processing chamber are subsequently introduced into the reacting region of the processing chamber to react with the Ir-based material. The distance between the generating and reacting region may be varied depending on the etch requirements and the specific system variables involved. By way of illustration, such distance may for example be on the order of from about 8 mm to about 600 mm dependent on the active life of the radicals.

Some radicals are long-lived and are capable of surviving many collisions (with other particles and the walls of the chamber) while maintaining sufficient energy to reach the reacting region. Other radicals are not as stable, and as such decay before reaching the reacting region. As a result, when using a mixture of gases containing both long- and short-lived radicals, the distance between the generating and reacting regions will desirably be adjusted accordingly. Advantageously, in the present invention, the use of $C_2F_6$ as a source material for the etchant medium tends to extend the active life of the $O_2$ radicals, thereby accommodating the provision of a moderate distance between the generating and reacting regions, e.g., a spacing distance in the range of from about 150 mm to about 600 mm.

In the microwave processing system, the plasma is typically generated in the preferred gas mixture of $C_2F_6$ and $O_2$ at a pressure in the range of from about 0.005 Torr to about 2 Torr by electromagnetic radiation having a frequency in the range of from about $1\times10^8$ Hz to about $1\times10^{12}$ Hz.

If an RF processing system is utilized, the plasma is typically generated by electromagnetic radiation having a frequency in the range of from about $1\times10^3$ Hz to about $1\times10^{12}$ Hz, more preferably in a range from about $1\times10^5$ Hz to about $1\times10^8$ Hz, and most preferably, the electromagnetic radiation is about 400 KHz.

The process gas mixture and processing conditions required to etch the Ir-based material typically depend on the etching features and shape of the product structure. The time and contacting conditions advantageously employed in a specific end use application of the invention may be readily determined by those of ordinary skill in the art, by the simple expedient of empirical determination of the etching of the deposited Ir-based (or other noble metal-based) material while varying the time and/or contacting conditions such as temperature, pressure, concentration of the etching agent, etc., to provide the desired results.

Generally, the process gas mixture comprising $C_2F_6$ and $O_2$ gases is introduced into the plasma processing system continuously at a suitable flow rate to maintain a continuous source of energized radicals. Typically, a suitable flow rate for the introduction of the gases into the plasma generating region ranges from about 200 sccm to about 1000 sccm, however, actual flow rates will be dependent on the volume of the reactor chamber and as such the above flow rates are illustrative only, and are not to be limitingly construed.

During the etching process, the Ir-based substrate may suitably be maintained at an appropriate temperature, e.g., a temperature ranging from about 0° C. to about 100° C., and more preferably from about 20° C. to about 50° C.

The plasma energized halogenated organic compounds may further comprise the reaction product of an initial reaction, e.g., reacting $C_2F_6$ with $O_2$ to form $COF_2$.

In one embodiment, at least one halogenated compound selected from an organic compound, such as $C_2F_6$; inorganic halogenated compound, such as $XeF_2$, $SF_6$; $SiF_4$, $Si_2F_6$, $Si_2OF_6$, and radicals $SiF_2$ and $SiF_3$; or mixture of halogenated organic and inorganic compounds, such as $C_2F_6$ and $XeF_2$ may be used as a gas-phase reactive halide composition or an etching gas to assist in the volatilization and removal of a noble metal, such as an iridium species from an iridium-based material deposited on a substrate.

In another embodiment, at least one halogenated compound selected from an organic halogenated compound, such as $C_2F_6$; inorganic halogenated compound, such as $XeF_2$ and $SF_6$ or a mixture of halogenated organic and inorganic compounds, such as $C_2F_6$ and $XeF_2$ may be used as an etching gas wherein the halogenated compound is reacted with elemental silicon or quartz substrates in the presence of $O_2$ or $O_3$, and the resultant active products, including for example, $SiF_4$, $Si_2F_6$, $Si_2OF_6$, and radicals $SiF_2$ and $SiF_3$, may be used as an etching gas, to assist in the volatilization and removal of iridium species from the iridium-based material on the substrate. Radicals $SiF_2$ and $SiF_3$ may further be generated by passing $SiF_4$ through an energetic dissociation source, wherein the energetic dissociation source is selected from the group consisting of a plasma source, an ion source, an ultra violet source and a laser source.

Preferably, the etching gas compositions lack nitrogen- and/or phosphorous-containing compounds, such as nitrogen- and/or phosphorous-containing -acceptor ligands to prevent interaction of the -acceptor ligands with the silicon or etching surface. When the silicon-containing active species are generated by interaction with the halogenated organic and/or inorganic compounds during the etching process, it is believed that highly volatized iridium species are formed that may include iridium-silicon halide complexes that are generally described as $IrX_1$, $IrX_3$, /$IrX_4$ and/or $IrX_6$ (where X=silicon halide complex), and more specifically $Ir(SiF_2)_x$, where x=1, 2, 3 or 4, such as $IrSi_2F_4$, $IrSi_3F_6$ and/or $IrSi_4F_6$. It is believed that if the etching composition comprises nitrogen- and/or phosphorous-containing species, such as nitrogen-and/or phosphorous-containing -acceptor ligands, that are in proximity to the etching surface the nitrogen-and/or phosphorous-containing species will interact with other components in the composition or with the resultant volatized species and reduce the effectiveness of the etching or the volatility of the volatized species.

In another aspect of the invention, iridium may be removed from a microelectronic device structure by contacting the microelectronic device structure with a gas-phase reactive halide comprising $XeF_2$ and an agent to assist in volatilizing, such as a Lewis-based adduct or electron backbonding species. The agent is selected from the group consisting of carbon monoxide, trifluorophosphine, and trialkylphosphines to accelerate the rate of etching by enhancing the volatility of the etch by-products and noble metal (halide)$_x$ species or noble metal (halide radical)x species.

The microelectronic device structure is contacted with the reactive halide and agent for a sufficient time to at least partially removing the iridium metal residue from the microelectronic device structure.

In yet another aspect of the invention, the iridium-containing film prior to its formation, as an electrode structure, may have deposited thereon a high temperature dielectric and/or ferroelectric material. This is usually accomplished in an oxidizing environment. As such the oxidizing ambient environment may be employed not only during deposition of the oxide dielectric/ferroelectric, but may also be used during the subsequent etching process for forming the electrode structure.

In addition to the etching of a deposited Ir-based material as an Ir-based electrode structure, it is contemplated that etching processes in accordance with the present invention may be used to clean an Ir CVD chamber to reduce particle formation and contamination therein.

The etching methods of the present invention may also be employed in etching Ir-based material deposited on or over a high temperature dielectric material or ferroelectric material, so that the Ir-based material serves as a top electrode structural material, as well as a hard mask layer to pattern the underlying dielectric or ferroelectric material.

The dielectric or ferroelectric material may comprise any suitable material for the specific end use or application being contemplated. Examples of potentially useful materials include SBT, PZT, BST, PLZT, PNZT, and $LaCaMnO_3$.

The etching methods of the present invention may be utilized for iridium films deposited for the formation of electrode and other elements of semiconductor devices, such as for example DRAMs, FRAMs, hybrid systems, smart cards and communication systems, as well as any other applications in which the thin films of iridium and/or iridium oxide, or combinations thereof, are advantageously employed.

The features and advantages of the invention are more fully shown by the following non-limiting example. This example illustrates one embodiment of the present invention involving etching of Ir-based materials deposited on a substrate to form Ir-based material structures thereon. As discussed hereinabove, methods in accordance with the present invention may be usefully employed to form etched metal structures deriving from a variety of noble metal-based materials.

EXAMPLE 1

An Ir-based material layer approximately 40 nm thick was deposited on a quartz crystal microbalance disk and placed on a support in the reacting chamber of a downstream microwave processing system.

A mixture of process gases including $C_2F_6$ and $O_2$ in a volumetric flow ratio (such ratio being a dimensionless value, wherein the volumetric flow rate of each of the respective halocarbon and oxidant gases is measured in the same units, e.g., of standard ft$^3$/minute) of 1 was continuously introduced into the microwave plasma generating region at a flow rate of approximately 1,100 sccm.

A plasma was formed from the process gases using a microwave plasma generator and the resultant plasma then was introduced into the reacting region of the plasma system. The etching process was performed for approximately 25 minutes, which was a sufficient time to completely remove the Ir-based material from the quartz crystal microbalance substrate.

While the invention has been described herein with reference to specific features, aspects and embodiments, it will be recognized that the invention may be widely varied, and that numerous other variations, modifications and other embodiments will readily suggest themselves to those of ordinary skill in the art. Accordingly, the ensuing claims are to be broadly construed, as encompassing all such other variations, modifications and other embodiments, within their spirit and scope.

What is claimed is:

1. A plasma-assisted dry etching method for etching an Ir-based noble metal material, said method comprising:

contacting the Ir-based noble metal material with an energized plasma composition comprising an etching species mixture for sufficient time to at least partially etch said Ir-based noble metal material, wherein the etching species mixture comprises (i) at least one halogenated compound selected from the group consisting of organic halogenated compounds, inorganic halogenated compounds and mixtures thereof, and (ii) an oxidizing agent selected from the group consisting of $O_2$ and $O_3$ gases, wherein the volumetric ratio of said at least one halogenated compound over said oxidizing agent is in a range of from about 4 to about 0.5, and wherein the energized plasma composition contacting the Ir-based noble metal material lacks nitrogen- and phosphorous-containing species.

2. The method according to claim 1, wherein the etch species mixture comprises $C_2F_6$ and $O_2$.

3. The method according to claim 2, wherein the volumetric ratio of $C_2F_6$ over O is about 1.

4. The method according to claim 1, wherein the energized plasma is energized by electromagnetic radiation.

5. The method according to claim 4, wherein the electromagnetic radiation has a frequency ranging from about $1 \times 10^3$ to about $1 \times 10^{12}$ Hertz.

6. The method according to claim 4, wherein the Ir-based noble metal material comprises $IrO_2$.

7. The method according to claim 1, wherein the energized plasma is energized in a downstream microwave processing system.

8. The method according to claim 7, further comprising the removing at least one iridium product in the course of the etching process.

9. The method according to claim 1, wherein the halogenated organic compound comprises a compound selected from to group consisting of $C_2F_6$, $C_2Cl_3F_3$, $C_4F_5$, $C_5F_8$, $C_3F_8$, $C_2Cl_2F_4$, $C_2ClF_3$, $CClF_3$, $CCl_3F$ and $CCl_2F_2$.

10. The method according to claim 1, wherein the Ir-based noble metal material is deposited on a high temperature dielectric material or ferroelectric material.

11. A plasma-assisted dry etching method for etching an Ir-based noble metal material, said method comprising:

contacting the Ir-based noble metal material with an energized plasma composition comprising an etching species mixture for sufficient time to at least partially etch said Ir-based noble metal material, wherein the etching species mixture comprises $XeF_2$, and wherein the energized plasma composition contacting the Ir-based noble metal material lacks nitrogen- and phosphorous-containing species.

12. A plasma-assisted dry etching method for etching an Ir-based noble metal material, said method comprising:

contacting the Ir-based noble metal material with an energized plasma composition comprising an etching species mixture for sufficient time to at least partially etch said Ir-based noble metal material, wherein the etching species mixture comprises (i) at least one halogenated compound selected from the group consisting of organic halogenated compounds, inorganic halogenated compounds and mixtures thereof, (ii) an oxidizing agent selected from the group consisting of oxygen and ozone, and (iii) a co-reactant to assist in the volatilization and removal of iridium products from the Ir-based noble metal material, and wherein the energized plasma composition contacting the Ir-based noble metal material lacks nitrogen- and phosphorous-containing species.

13. The method according to claim 12 wherein the co-reactant precursor is selected from the group consisting of elemental silicon and quartz.

14. A plasma-assisted dry etching method for etching an Ir-based noble metal material, said method comprising:

contacting the Ir-based noble metal material with an energized plasma composition comprising an etching species mixture for sufficient time to at least partially etch said Ir-based noble metal material, wherein the etching species mixture comprises (i) a halogenated organic compound $C_2F_6$, (ii) a halogenated inorganic compound $XeF_2$, and (iii) an oxidizing gas selected from the group consisting of oxygen and ozone, and wherein the energized plasma composition contacting the Ir-based noble metal material lacks nitrogen- and phosphorous-containing species.

15. The method according to claim 14, wherein the energized plasma further comprises reactive species formed by reacting $C_2F_6$ with elemental silicon.

16. The method according to claim 15, wherein the oxidizing gas comprises $O_2$.

17. The method according to claim 15, further comprising the removal of at least one iridium product during the etching process.

18. The method according to claim 17, wherein the at least one iridium product comprises an iridium-containing composition selected from the group consisting of $IrSi_2F_4$, $IrSi_2F_6$, and $IrSi_4F_6$.

19. A method of fabricating a microelectronic device structure, comprising:

(a) depositing an Ir-based noble metal material on a substrate;

(b) forming a pattern on the deposited Ir-based noble metal material of a desired configuration;

(c) contacting the deposited Ir-based noble metal material with an energized plasma comprising an etching species mixture, to thereby etch the Ir-based noble metal material, wherein the etching species mixture comprises (i) at least one halogenated compound selected from the group consisting of organic halogenated compounds, inorganic halogenated and mixtures thereof, and (ii) an oxidizing agent selected from the group consisting of $O_2$ and $O_3$ gases, wherein the volumetric ratio of said at least one halogenated compound over said oxidizing agent is in a range of from about 4 to about 0.5, and wherein the energized plasma composition contacting the noble metal material lacks nitrogen-and phosphorous-containing species; and (d) continuing step (c) for a sufficient time and under sufficient conditions to form the microelectronic device structure or a precursor thereof.

20. The method according to claim 19, wherein the electromagnetic radiation has a frequency ranging from about $1 \times 10^3$ to about $1 \times 10^{12}$ Hertz.

21. The method according to claim 19, wherein the halogenated organic compound comprises a compound selected from the group consisting of $C_2F_6$, $C_2Cl_3F_3$, $C_4F_8$, $C_5F_8$, $C_3F_8$, $C_2Cl_2F_4$, $C_2ClF_3$, $CClF_3$, $CCl_3F$ and $CCl_2F_2$.

22. The method according to claim 19, wherein the halogenated organic compound comprises $C_2F_6$.

23. The method according to claim 19, wherein the etch species mixture comprise $C_2F_6$ and $O_2$.

24. The method according to claim 23, wherein the energized plasma is energized by electromagnetic radiation.

25. The method according to claim 23, wherein the volumetric ratio of $C_2F_6$ over $O_2$ is about 1.

26. A method of fabricating a microelectronic device structure, comprising:
   (a) depositing an Ir-based noble metal material on a substrate;
   (b) forming a pattern on the deposited Ir-based noble metal material of a desired configuration;
   (c) contacting the deposited Ir-based noble metal with an energized plasma comprising an etching species mixture, to thereby etch the Ir-based noble metal material, wherein the etching species mixture comprises (i) at least one halogenated compound selected from the group consisting of organic halogenated compounds, inorganic halogenated and mixtures thereof, (ii) an oxidizing agent selected from the group consisting of oxygen and ozone, and (iii) a co-reactant to assist in volatilization and removal of iridium products from the Ir-based noble metal material, wherein the co-reactant is selected from the group consisting of elemental silicon and quartz, and wherein the energized plasma composition contacting the Ir-based noble metal material lacks nitrogen- and phosphorous-containing species; and
   (d) continuing step (c) for a sufficient time and under sufficient conditions to form the microelectronic device structure or a precursor thereof.

27. The method according to claim 26, further comprising removing at least one iridium product during the etching process.

28. A method of fabricating a microelectronic device structure, comprising:
   (a) depositing an Ir-based noble metal material on a substrate;
   (b) forming a pattern on the deposited Ir-based noble metal material of a desired configuration;
   (c) contacting the deposited Ir-based noble metal material with an energized plasma comprising an etching species mixture, to thereby etch the Ir-based noble metal material, wherein the etching species mixture comprises $XeF_2$, and wherein the energized plasma composition contacting the Ir-based noble metal material lacks nitrogen-and phosphorous-containing species; and
   (d) continuing step (c) for a sufficient time and under sufficient conditions to form the microelectronic device structure or precursor thereof.

29. A method of fabricating a microelectronic device structure, comprising:
   (a) depositing an Ir-based noble metal material on a substrate;
   (b) forming a pattern on the deposited Ir-based noble metal material of a desired configuration;
   (c) contacting the deposited Ir-based noble metal material with an energized plasma comprising an etching species mixture, to thereby etch the Ir-based noble metal material, wherein the etching species mixture comprises (i) $C_2F_6$, and (ii) reactive species formed by reacting $C_2F_6$ with a co-reacting species selected from the group consisting of elemental silicon and quartz and wherein the energized plasma composition contacting the Ir-based noble metal material lacks nitrogen-and phosphorous-containing species; and
   (d) continuing step (c) for a sufficient time and under sufficient conditions to form the microelectronic device structure or a precursor thereof.

30. The method according to claim 29, further comprising removal of at least one iridium product in the etching process.

31. The method according to claim 30, wherein the at least one iridium product comprises an iridium composition selected from the group consisting of $IrSiF_3$, $IrSi_2F_4$, $IrSi_3F_6$, and $IrSi_4F_6$.

32. A method for removing a noble metal residue from a microelectronic device structure, the method comprising:
   contacting the microelectronic device, having deposited thereon a noble metal residue selected from the group consisting of platinum, palladium, iridium and rhodium, with a gas-phase reactive composition comprising (i) a halide component selected from the group consisting of $SF_6$, $SiF_4$, $Si_2F_6$, $SiF_2$ radical and $SiF_3$ radical, and (ii) an oxidizing gas selected from the group consisting of $O_2$ and $O_3$ gases, in an amount to remove noble metal residue from the microelectronic device structure, wherein the volumetric ratio of said halide component over said oxidizing gas is in a range of from about 4 to about 0.5, and wherein the gas-phase reactive composition lacks nitrogen-and phosphorous-containing species.

33. The method according to claim 32, wherein the halide is selected from the group consisting of $SiF_2$ and $SiF_3$ radicals and the halide is generated by passing $SiF_4$ through an energetic dissociation source.

34. The method according to claim 33, wherein the energetic dissociation source is selected from the group consisting of plasma sources, ion sources, ultraviolet sources and laser sources.

35. The method according to claim 32, wherein the halide is selected from the group consisting of $SiF_2$ and $SiF_3$ radicals.

36. The method according to claim 32, wherein the halide is selected from the group consisting of $SF_6$, $SiF_4$, and $Si_2F_6$.

37. The method according to claim 32, wherein the halide comprises $SF_6$.

38. A method for removing a noble metal residue from a microelectronic device structure, the method comprising:
   contacting the microelectronic device, having deposited thereon a noble metal residue selected from the group consisting of platinum, palladium, iridium, and rhodium, with a gas-phase reactive composition comprising (i) a halide component selected from the group consisting of $SiF_2$ and $SiF_3$ radicals generated by reaction of $XeF_2$ with silicon, and (ii) an oxidizing gas selected from the group consisting of oxygen and ozone, in an amount to remove noble metal residue from the microelectronic device structure, wherein the gas-phase reactive composition lacks nitrogen-and phosphorous-containing species.

39. A method for removing from a microelectronic device structure, a noble metal residue comprising iridium, the method comprising:
   contacting the microelectronic device structure with a gas-phase reactive halide comprising $XeF_2$ and an agent to assist in volatilizing and at least partially removing the noble metal residue from the microelectronic device structure.

40. The method according to claim 39, wherein the agent is selected from the group consisting of Lewis bases and electron back-bonding species.

41. The method according to claim 39, further comprising disposing the microelectronic device structure in a chamber and introducing a gas phase reactive halide composition selected from the group consisting of $SF_6$, $SiF_4$ and $Si_2F_6$ that is continuously flowed through the chamber, in combination with an energetic dissociation source selected from the group consisting of plasma sources, ion sources, ultraviolet sources and laser sources.

42. The method according to claim 39, further comprising disposing the microelectronic device structure in a chamber and introducing a gas phase reactive halide composition selected from the group consisting of $SiF_2$ and $SiF_3$ that is continuously flowed through the chamber, in combination with an energetic dissociation source selected from the group consisting of plasma sources, ion sources, ultraviolet sources and laser sources.

43. The method according to claim 39, wherein the agent is selected from the group consisting of carbon monoxide, trifluorophosphine, and trialkylphosphines.

44. The method according to claim 43, wherein the agent further comprises an iridium halide species selected from the group consisting of $Ir(X)_1$, $Ir(X)_3$, $Ir(X)_4$ and $Ir(X)_6$, wherein X represents the halide of the reactive halide composition.

45. The method according to claim 39, wherein the gas-phase reactive halide composition further comprises a gas phase reactive halide species selected from the group consisting of $SiF_4$, $Si_2F_6$, $SiF_2$ radical and $SiF_3$ radical; and the microelectronic device structure is further contacted with an agent to assist in volatilizing and removing the noble metal residue on the microelectronic device structure.

46. A method for removing from a microelectronic device structure a noble metal residue including at least one metal selected from the group consisting of platinum, palladium, iridium and rhodium, the method comprising:
contacting the microelectronic device structure with a gas-phase reactive composition comprising: (i) $SiF_4$ in a sufficient amount to at least partially remove noble metal residue, and (ii) an oxidizing gas selected from the group consisting of $O_2$ and $O_3$ gases,
wherein the volumetric ratio of $SiF_4$ over said oxidizing gas is in a range of from about 4 to about 0.5.

47. A method for removing from a microelectronic device structure a noble metal residue including at least one metal selected from the group consisting of platinum, palladium, iridium and rhodium, the method comprising:
contacting the microelectronic device structure with a gas-phase reactive halide composition comprising (i) $Si_2F_6$ in a sufficient amount to at least partially remove noble metal residue, and (ii) an oxidizing gas selected from the group consisting of $O_2$ and $O_3$ gases,
wherein the volumetric ratio of $Si_2F_6$ over said oxidizing gas is in range of from about 4 to about 0.5.

48. A method for removing from a microelectronic device structure a noble metal residue including at least one metal selected from the group consisting of platinum, palladium, iridium and rhodium, the method comprising contacting the microelectronic device structure with a gas-phase reactive composition comprising: (i) a halide component selected from the group consisting of $SF_6$, $SiF_4$, $Si_2F_6$, $SiF_2$ radical, $SiF_3$ radical, and $XeF_2$, in an amount effective to at least partially remove the noble metal residue, and (ii) an oxidizing gas selected from the group consisting of $O_2$ and $O_3$, wherein the volumetric ratio of said halide component over said oxidizing gas is in a range of from about 4 to about 0.5, and wherein said gas-phase reactive composition a nitrogen- and phosphorous-containing species.

* * * * *